(12) United States Patent
Høgsaa et al.

(10) Patent No.: US 9,137,983 B2
(45) Date of Patent: Sep. 22, 2015

(54) DISPENSING UNIT (71) Applicant: Aalborg Universitet, Aalborg Ø (DK)

(72) Inventors: Asger Hangstrup Høgsaa, Aalborg (DK); Bjarke Hangstrup Høgsaa, Aalborg (DK); Sebastian André Jensen Langhoff, Aalborg (DK)

(73) Assignee: AALBORG UNIVERSITET, Aalborg O (DK)

( * ) Notice: Subject to any disclaimer, the term of this patent is extended or adjusted under 35 U.S.C. 154(b) by 0 days.

(21) Appl. No.: 14/366,131

(22) PCT Filed: Dec. 14, 2012

(86) PCT No.: PCT/DK2012/050468
§ 371 (c)(1),
(2) Date: Jun. 17, 2014

(87) PCT Pub. No.: WO2013/091640
PCT Pub. Date: Jun. 27, 2013

(65) Prior Publication Data
US 2014/0356953 A1    Dec. 4, 2014

(30) Foreign Application Priority Data

Dec. 22, 2011 (EP) .................. 11195204

(51) Int. Cl.
*A01N 1/02* (2006.01)
*A61B 10/00* (2006.01)
*B01L 3/02* (2006.01)
*B01L 3/00* (2006.01)

(52) U.S. Cl.
CPC .......... *A01N 1/0242* (2013.01); *A61B 10/0096* (2013.01); *B01L 3/0293* (2013.01);

(Continued)

(58) Field of Classification Search
CPC ...... A01N 1/0242; B01L 3/0293; B01L 3/523
See application file for complete search history.

(56) References Cited

U.S. PATENT DOCUMENTS

2005/0160701 A1    7/2005 Stevens

FOREIGN PATENT DOCUMENTS

DE    20 2009 013 304 U1    1/2010
EP    1 816 461 A1    8/2007

(Continued)

OTHER PUBLICATIONS

International Search Report for PCT/DK2012/050468 dated Apr. 4, 2013.

*Primary Examiner* — Sam P Siefke
(74) *Attorney, Agent, or Firm* — Knobbe Martens Olson & Bear LLP (57) ABSTRACT The invention relates to a dispensing unit for dispensing fluid into an external container. The dispensing unit comprises: a connector, a reagent cylinder for storing the fluid, and a locking ring. The connector comprises an upper fastener, and a bottom wall with at least one passage therethrough. The reagent cylinder comprises at least one compartment for storing the fluid, which compartment comprises at least one opening through a cylinder bottom. The at least one opening is located so that for at least one mutual orientation of the reagent cylinder and the connector, fluid can flow from the compartment to the external container via the at least one opening and the at least one passage. The locking ring comprises a second fastener which fastens to the upper fastener of the connector, so that when the locking ring is tightened, the reagent cylinder is pressed towards the interior bottom of the connector.

13 Claims, 6 Drawing Sheets (52) U.S. Cl.
CPC ......... *B01L 3/52* (2013.01); *B01L 3/523* (2013.01);
*B01L 3/527* (2013.01); *B01L 2200/025*
(2013.01); *B01L 2200/0689* (2013.01); *B01L*
*2200/16* (2013.01); *B01L 2300/0832* (2013.01);
*B01L 2400/0644* (2013.01)

(56) References Cited

FOREIGN PATENT DOCUMENTS

| WO | WO 99/33501 A1 | 7/1999 |
| WO | WO 2008/040812 A1 | 4/2008 |
| WO | WO 2009/038763 A1 | 3/2009 |

DISPENSING UNIT

CROSS REFERENCE TO RELATED APPLICATIONS

This application is a U.S. National Phase Application of PCT International Application No. PCT/DK2012/050468, filed on Dec. 14, 2012, designating the United States of America and published in the English language, which is an International Application of and claims the benefit of priority to European Patent Application No. 11195204.0, filed on Dec. 22, 2011. The disclosures of the above-referenced applications are hereby expressly incorporated by reference in their entireties.

FIELD OF THE INVENTION

The present invention relates to a dispensing unit for dispensing fluid into an external container, and in particular a dispensing unit wherein the dispensing involves manual rotation of parts of the dispensing unit relative to each other.

BACKGROUND OF THE INVENTION

Preservation of human or animal tissue samples for analysis is traditionally performed by the use of toxic preservation fluids which have to be treated with special care. At the same time, a rapid immersion of the tissue sample is essential for maintaining as many of the characteristic tissue sample properties as possible for structural and molecular analysis. It is therefore important to be particularly attentive to the handling of the toxic preservation fluid, since there is a risk that a potentially hasty use of toxic fluids may give stressful and dangerous situations. Prolonged or repeated contact with preservation fluids may result in development of respiratory impairment or chronic respiratory inflammations such as asthma or chronic bronchitis. A single accidental spill involving an exposure to a high concentration of preservation fluid may also result in respiratory impairment due to the toxic fumes that some preservation fluids produce. Furthermore, there is also a risk of eye damages if a person gets the preservation fluid in the eyes. Therefore, the preservation fluids are traditionally handled using a fume cupboard, gloves, and goggles or other types of complete eye protection. If the surgery room does not contain a fume cupboard, the tissue samples taken during surgery need to be transported to another room or location which results in a delay and an extra need for cleaning of the person involved. These factors are time consuming and prolong the time for immersing the tissue sample into a preservation fluid; such delay is disadvantageous as it may cause damage to the tissue sample.

Furthermore, not all medical clinics have a fume cupboard, and this may hinder the clinics in being able to perform even small biopsies, such as skin biopsies, due to the toxic danger of the preservation fluid; or it may force some clinics to perform the biopsies nevertheless which involves a great risk.

When handling large volumes of sample, such as an intestine, that needs to be preserved, a large volume of preservation fluid is required, and this can be unwieldy and thereby dangerous due to the risk of toxicity if accidents occur.

Hence, a device for handling the preservation fluid without the risk of having contact with the preservation fluid would be advantageous, and in particular a more efficient and reliable device for dispensing the preservation fluid rapidly and without risk would be advantageous.

Certain biological procedures, such as water sample analysis, may involve dispensing of different fluids that need to be dispensed in accurate amounts and in a certain order, and may furthermore involve components as inhibitors and toxins. These analyses are therefore time consuming and may even lead to unsuccessful results due to incorrectly followed procedures; they may additionally constitute a risk for the person performing the analysis. For this type of analyses it would therefore be advantageous to obtain a dispensing device that is easier to use and with a lower risk of incorrectly followed procedures, including using incorrect amounts of fluids. For some, but not all, of these types of analyses, it will furthermore be advantageous to obtain a device for handling the preservation fluid without the risk of having contact with the preservation fluid.

OBJECT OF THE INVENTION

Thus it is an object of the present invention to provide a dispensing unit that solves at least some of the above mentioned problems of the presently used methods with respect to handling fluids to be dispensed into an external container.

It is an object of the present invention to provide a dispensing unit that is more efficient and easy to use than presently used containers and methods. It is an object of some embodiments of the invention to provide a dispensing unit with which it is possible to dispense preservation fluid into an external container without the risk of having direct contact with the toxic preservation fluid.

It is an object of some embodiments of the invention to provide an efficient and reliable device for adding more than one type of fluid either simultaneously or one fluid at the time.

It is a further object of the present invention to provide an alternative to the prior art.

SUMMARY OF THE INVENTION

Thus, the above described object and several other objects are intended to be obtained in a first aspect of the invention by providing a dispensing unit for dispensing fluid into an external container, comprising
    a connector part comprising
        upper fastening means, and
        a bottom wall having an interior bottom surface, an exterior bottom surface, and at least one passage between the interior bottom surface and the exterior bottom surface,
    a reagent cylinder for storing the fluid, the reagent cylinder being adapted to be rotatably fitted into the connector part, and comprising
        a cylinder bottom, and
        at least one compartment for storing the fluid, the compartment comprising at least one opening through the cylinder bottom, wherein the at least one opening is located so that for at least one mutual orientation of the reagent cylinder and the connector part, the at least one opening is aligned with the at least one passage, and fluid can flow from the compartment to the external container via the at least one opening and the at least one passage,
    a locking ring comprising
        fastening means adapted to be fastened to the upper fastening means of the connector part, so that when the locking ring is tightened, the cylinder bottom of the reagent cylinder is pressed towards the interior bottom surface of the connector part and creating a fluid tight sealing between the connector part and the reagent cylinder.

"Rotatably fitted into" is preferably used to mean that an item A is placed into, such as in an inner cavity of another item B, and within that item B it is possible to rotate item A relative to item B.

The external container may e.g. be configured for holding a tissue sample.

The reagent cylinder may comprise more than one compartment for storing one or more types of fluid. This may e.g. be advantageous for certain biological analyses where dispensing of different fluids is required. If the reagent cylinder comprises more than one compartment, they may be of the same or different size and/or shape.

In some embodiments of the invention, the connector part has the at least one passage arranged so that it is possible to dispense fluid from one compartment at a time. This may e.g. be advantageous in situations where the analysis requires that there is a period of time between dispensing the fluids from the different compartments, or if the reagents may not be mixed before use and/or has to be dispensed in a particular order.

Each compartment may comprise two openings through the cylinder bottom. At least for some dimensions of the openings, the use of two openings will facilitate the flow of fluid, since an outlet of fluid requires intake of air into the compartment; this is improved by the use of two openings instead of just one.

In some embodiments of the invention, each compartment can comprise one sealing means arranged around the at least one opening of each compartment. The sealing means may e.g. be an O-ring which is arranged around the openings of each compartment and provides a fluid tight sealing between the connector part and the reagent cylinder, when the reagent cylinder is pressed against the connector part.

The connector part preferably comprises lower fastening means adapted to be fastened to the external container. This enables provision of a sealed unit comprising the dispensing unit and the external container, which sealed unit is suited for storing and transporting e.g. a tissue sample until further analysis is carried out. Furthermore this provision of a sealed unit thereby prevents outlet of toxic fumes to surroundings.

The lower fastening means of the connector part may be threads. This can be used for easy assembly with an external container having corresponding threads. Other types of fastening means may also be used, e.g. for assembly with a container not having threads. The fastening means may also be a snap-lock.

The upper fastening means of the connector part and the fastening means of the locking ring are preferably threads. This has the advantage that the locking ring can be tightened until a sealed connection between the connector part and the reagent cylinder is obtained. However, other types of fastening means are also covered by the scope of the present invention. Such fastening means could e.g. be a snap-lock, such as click system where the edge of one part has a matching edge on another part. When pressing mated edges of the two parts together, the elements will attach.

Each of the connector part, the reagent cylinder, and the locking ring may be made of one of the following materials:
Polymer, such as propylene or polyoxymethylene
Glass
Metal If one or more of the parts is/are made of metal, it could e.g. be stainless steel or any metal alloy that can serve as a container for a fluid. For some materials it will be possible to use transparent material. Hereby it can be visually inspected that the dispensing unit is appropriately assembled, including e.g. that O-rings are compressed so that a fluid tight sealing is ensured. It may also be advantageous to be able to check visually e.g. that all the fluid has been dispensed and that there is no leak e.g. due to a worn or damaged O-ring. For some applications it may be required to use a material which can be sterilized.

The connector part may comprise an outer circular wall forming a space into which the reagent cylinder can be fitted.

The reagent cylinder preferably comprises a top surface and may comprise a handle extending from the top surface, the handle being adapted to be used for manually rotating the reagent cylinder inside the connector part. By rotating the reagent cylinder relative to the connector part, the openings on the reagent cylinder are rotated relative to the passages on the connector part, and thereby it will be possible to control whether the fluid can flow from the reagent cylinder or not.

In some embodiments of the invention, the connector part further comprises a removable sealing covering the lower fastening means. It may also cover the exterior bottom surface as well. This sealing may be advantageous in keeping the bottom part of the dispensing unit clean before use. The sealing may also be advantageous in controlling if there has been any leakage from the dispensing unit before use.

In some embodiments of the invention, a reagent for preservation of tissue samples is stored in the at least one compartment so that the dispensing unit is ready for use.

A second aspect of the invention relates to a method for dispensing a reagent for preservation of tissue samples into a container comprising the tissue sample, the method comprising use of a dispensing unit as described above.

The first and second aspects of the present invention may each be combined. These and other aspects of the invention will be apparent from and elucidated with reference to the embodiments described hereinafter.

BRIEF DESCRIPTION OF THE FIGURES

Embodiments of the invention will be described in more detail in the following with regard to the accompanying figures. The figures show one way of implementing the present invention and is not to be construed as being limiting to other possible embodiments falling within the scope of the attached claim set.

FIG. 7.a is a cross sectional view along line A-A in FIG. 7.b, and FIG. 7.b is a cross sectional view along line B-B in FIG. 7.a.

DETAILED DESCRIPTION OF AN EMBODIMENT

Figure 1:
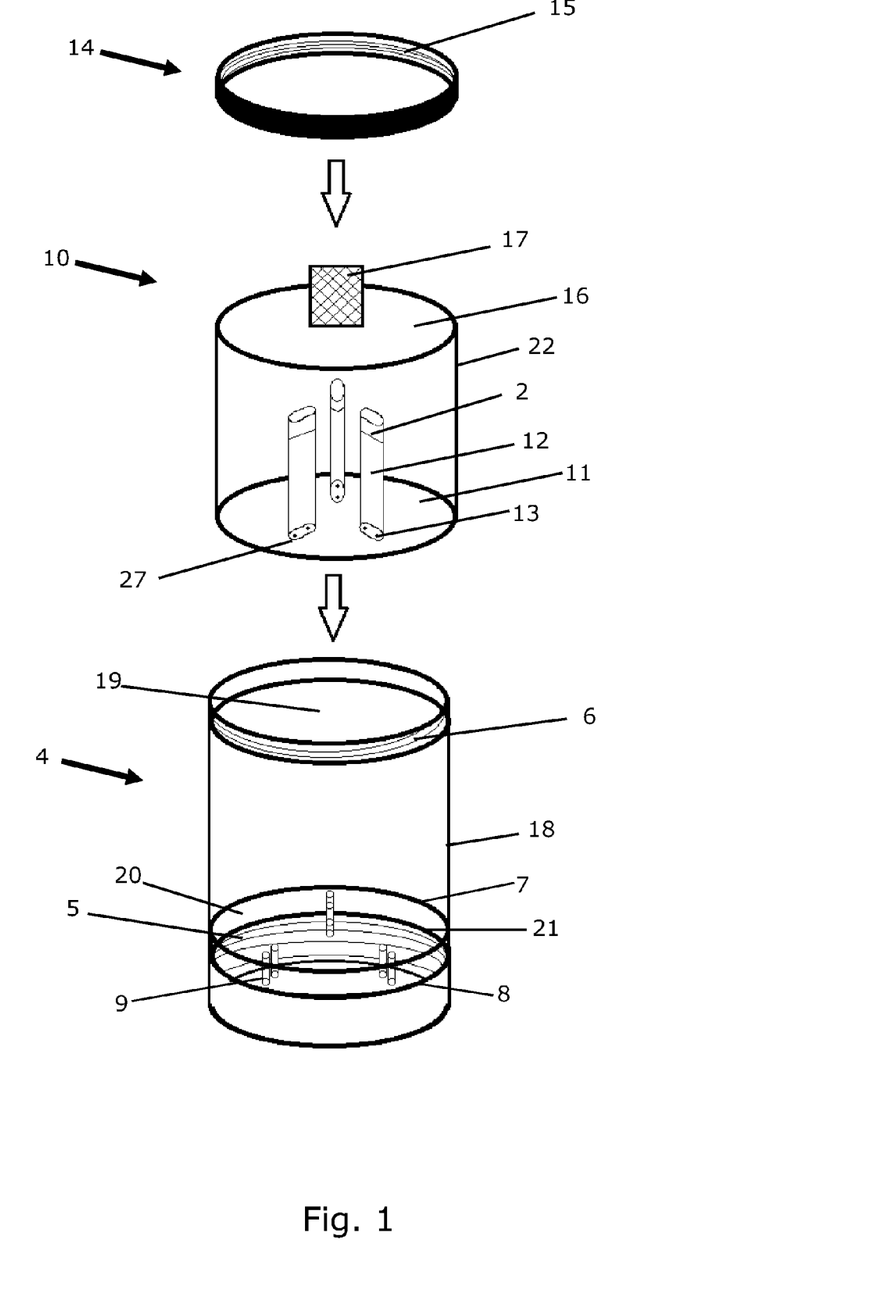
FIG. 1 shows an exploded view of an embodiment of the invention.

FIG. 1 shows an exploded view of an embodiment of a dispensing unit 1 according to the present invention. The dispensing unit 1 is intended for dispensing fluid 2 into an external container 3 (see FIG. 2). The dispensing unit 1 comprises three parts: A connector part 4, a reagent cylinder 10 and a locking ring 14. The dispensing unit is shown as made from transparent material to reveal the inner structures thereof.

The connector part 4 is cylindrically shaped and comprises an outer wall 18 and upper fastening means 6 which are illustrated as threads. The connector part 4 has a top opening 19 which is defined by the upper end of the outer wall 18. The connector part 4 further comprises a bottom wall 20 having an interior bottom surface 7, an exterior bottom surface 8, and six passages 9 between the interior bottom surface 7 and the exterior bottom surface 8. The six passages 9 are positioned in three pairs located between the centre of bottom wall 20 and the outer wall 18. There are no further openings between the bottom surface 7 and the outer wall 18, and consequently the six passages 9 are the only passages for fluid to pass through the bottom wall 20. The connector part 4 further comprises lower fastening means 5 which is illustrated as threads. The lower fastening means 5 is adapted to be fastened to the external container 3 (see FIG. 2). In order to keep a fluid tight sealing between the connector part and the external container, sealing means 21, which may be an O-ring, is preferably fastened along the circumference of the fastening means 5 up against the exterior bottom surface 8.

The reagent cylinder 10 shown in FIG. 1 is cylindrically shaped and defined by a cylinder wall 22, a cylinder bottom 11, and a top surface 16. It is adapted to be rotatably fitted in the connector part 4 through the top opening 19 of the connector part 4. In the embodiment shown on FIG. 1, the reagent cylinder 10 comprises three compartments 12 for storing fluid 2. Each compartment 12 comprises two openings 13 through the cylinder bottom 11. The two openings 13 are provided for inlet and outlet of fluid 2 as will be described in further detail below. The shape and size of the compartments are given for illustrative purposes only; they may vary significantly from what is illustrated in the figures.

The openings 13 are located so that they can be aligned with the passages 9 in the connector part 4. For some mutual orientations of the reagent cylinder 10 and the connector part 4, fluid 2 can flow from the compartments 12 to the external container 3 via the openings 13 and the passage 9. In order to avoid leakage of fluid, each compartment 12 comprises one sealing means 27 arranged around the two openings 13 of each compartment 12 on the exterior of the cylinder bottom 11. This has the effect of keeping a fluid tight sealing between the reagent cylinder 10 and the connector part 4 when they are pressed together as will be described in further detail below.

The reagent cylinder 10 comprises a handle 17 extending from the top surface 16, the handle 17 being adapted to be used for manually rotating the reagent cylinder 10 inside the connector part 4. The handle is shown schematically as a square; in practise it may have any desired shape such as being cylindrical. The handle 17 is shown as being provided with a rugged surface in order to provide a firm grip when rotating the reagent cylinder 10. By rotating the handle 17, the reagent cylinder 10 will rotate relative to the connector part 4, and accordingly it is possible to rotate the openings 13 on the reagent cylinder 10 relative to the passages 9 on the connector part 4. Thereby it is possible to control the flow of fluid from the compartment 12 to the external container 3 and control if the passage should be blocked or opened.

The locking ring 14 is provided with interior threads in order to fasten the locking ring onto the connector part 4 by engaging the threads on the interior of the locking ring 14 with the upper fastening means 6 of the connector part 4. As mentioned above, other types of fastening means may also be used.

Figure 2:
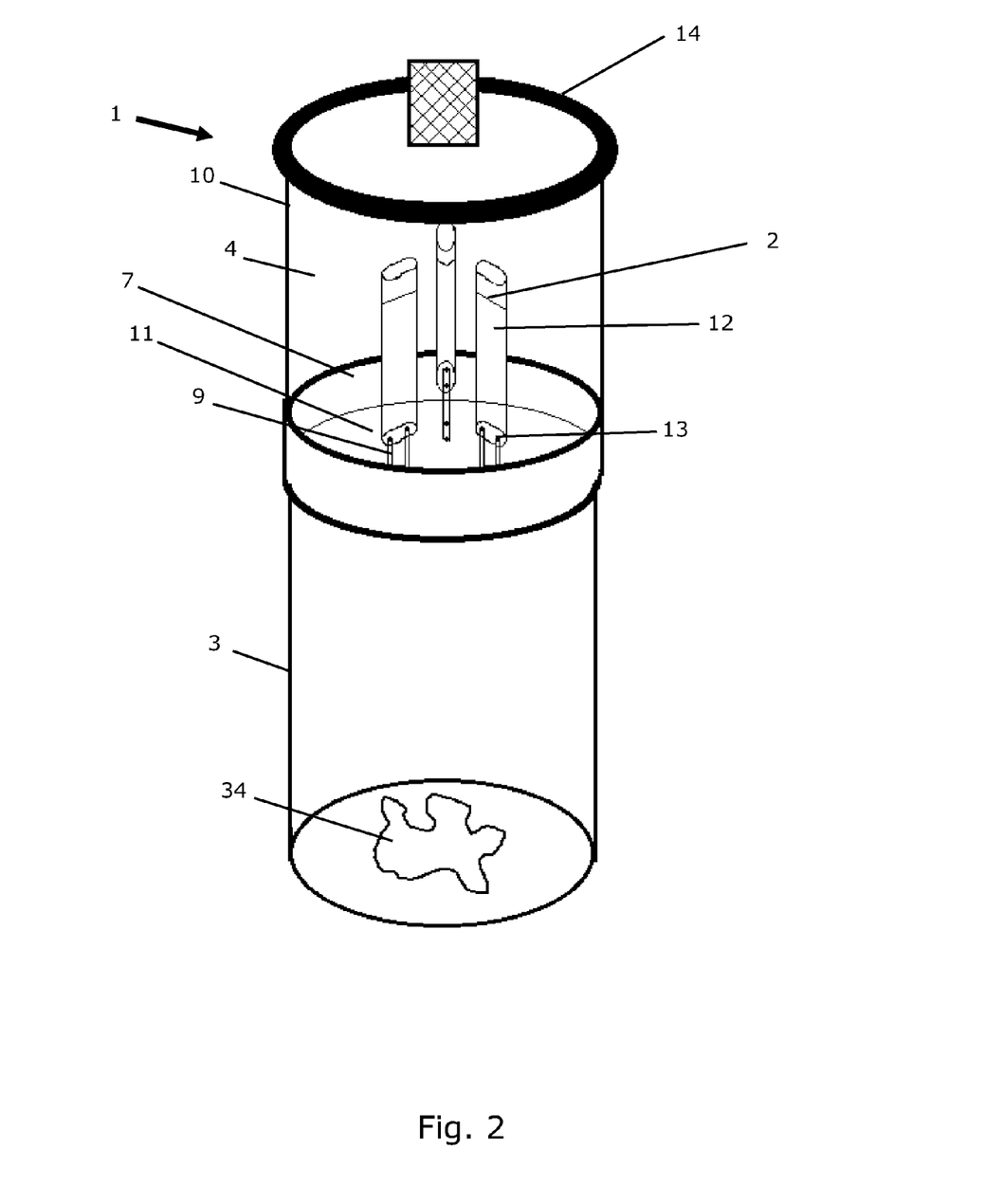
FIG. 2 shows an assembled view of the embodiment of the invention shown in FIG. 1.

FIG. 2 shows the embodiment of FIG. 1 in an assembled view and furthermore assembled to an external container 3 holding a tissue sample 34. When assembling the dispensing unit 1, the reagent cylinder 10 is placed inside the connector part 4, and thereafter the locking ring 14 is mounted on top of the reagent cylinder 10 and screwed into the connector part 4. When the locking ring 14 is tightened, the cylinder bottom 11 of the reagent cylinder 10 is pressed towards the interior bottom 7 of the connector part 4, thereby creating a fluid tight sealing between the connector part 4 and the reagent cylinder 10.

The compartments 12 are filled with the fluid 2 prior to mounting the dispensing unit 1 onto an external container 3. The prefilling of the compartments 12 with fluid 2 is preferably done automatically in mass production on a fabric, typically in a sterile environment. It is done by aligning the passages 9 of the connector part 4 with the openings 13 of the reagent cylinder 10 creating a flow passage from the passages 9 into the compartments 12, and hence a machine may inject the fluid 2 into the compartments 12 while holding the dispensing unit 1 upside down. Another way to perform the prefilling of the compartments 12 may be to fill them manually, preferably in a fume cupboard. This is also done by aligning the passages 9 of the connector part 4 with the openings 13 of the reagent cylinder 10 creating a flow passage from the passages 9 into the compartments 12 and by the use of e.g. a pipette filled with the fluid 2 while holding the dispensing unit 1 upside down. The fluid may be injected into the compartments 12 one at the time. After filling the compartments 12, the reagent cylinder 10 is rotated to a position where flow of fluid 2 from the reagent cylinder 10 is blocked.

Figure 3A:
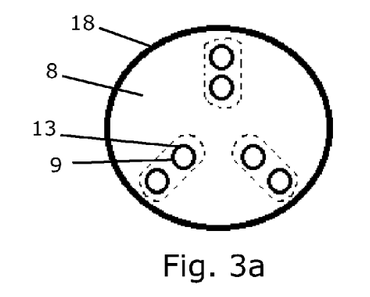
FIG. 3a shows a bottom view of the embodiment of the invention shown in FIG. 1 in an open position.
Figure 3B:
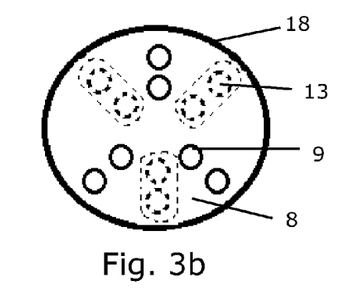
FIG. 3b shows a bottom view of the embodiment of the invention shown in FIG. 1 in a closed position.

FIGS. 3a and 3b show bottom views of the embodiment of FIG. 1. When the dispensing unit 1 is in a closed position as shown in FIG. 3.b, there is no flow passage from the compartments 12 of the reagent cylinder 10 to the passages 9 on the connector part 4. When rotating the reagent cylinder 10 from a closed position by the use of the handle 17, the openings 13 on the reagent cylinder 10 can be positioned so that the openings 13 are aligned with the passages 9, so that the dispensing unit 1 is in an open position as shown in FIG. 3.a. The fluid 2 can thereby flow from the compartments 12 via the openings 13 and through the passages 9. Since the fluid 2 flows due to gravitation, it is a precondition that the dispensing unit 1 is held with the bottom facing downwards when filling the fluid 2 into the external container 3. Correspondingly the dispensing unit 1 is held with the bottom facing upwards when dispensing fluid 2 into the compartments 12. In principle inclined orientations may also be used.

Figure 4:
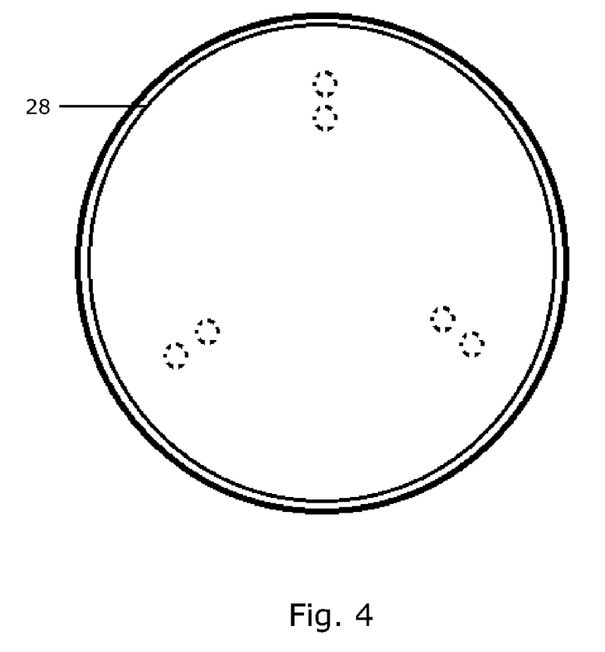
FIG. 4 shows a bottom view of an embodiment of the invention provided with a removable sealing.

In order to keep the bottom of the dispensing unit clean, the connector part 4 preferably comprises a removable sealing 28 covering the lower fastening means 5 as well as at least part of the exterior bottom surface 8. FIG. 4 shows a bottom view of an example of such an embodiment of the invention with removable sealing 28. Another important purpose of the removable sealing 28 is to control if there has been any leakage of fluid 2 after filling the compartments 12, and during a possible storage and transport of the dispensing unit 1 before use. The removable sealing 28 may e.g. be a thin circular shaped cover made of aluminium foil and fastened to the edge of the lower fastening 5 means and the outer wall 18 using any appropriate adhesive. The removable sealing 28 may preferably be attached to the dispensing unit 1 immediately after the prefilling of the compartments 12 in a sterile environment. The removable sealing 28 should stay attached during a possible transport or storage before use and should only be removed immediately before mounting the dispensing unit 1 to onto the external container 3 in order to control if there has been any leakage as well as keeping the bottom of the dispensing unit 1 clean.

Figure 5:
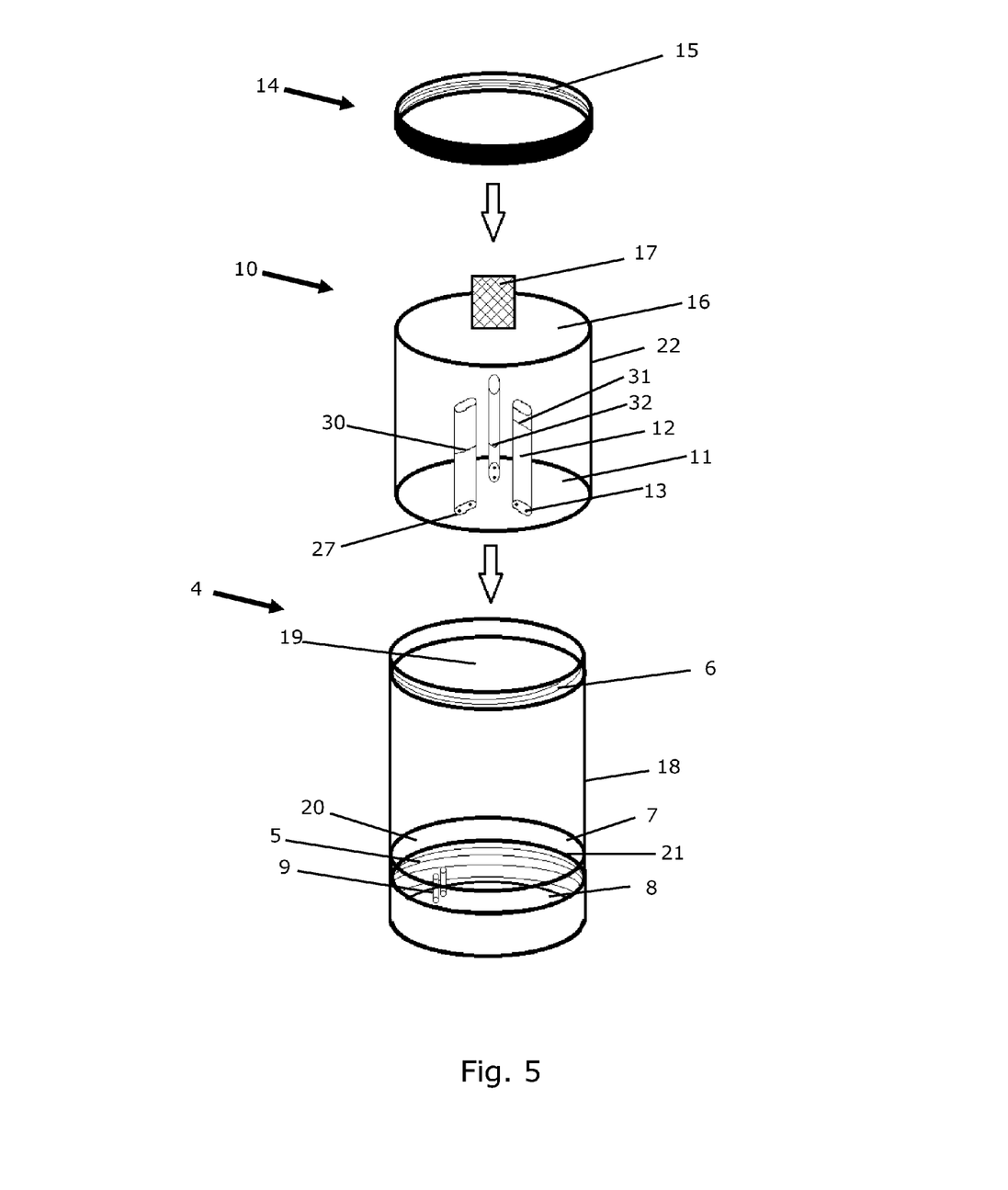
FIG. 5 shows an exploded view of another embodiment of the invention.

Another embodiment of the dispensing unit 1 can be seen in FIG. 5, in which the reference numbers used for similar components are the same as in the previous figures. The embodiment in FIG. 5 differs from the embodiment in FIGS. 1 to 4 in that the connector part 4 only has two passages 9 arranged in one pair, so that it is possible to dispense fluid 2 from one compartment 12 at a time. Furthermore the embodiment in FIG. 5 differs from the embodiment in FIGS. 1 to 4 in that the fluids 2 in the compartments 12 are different types of fluids 30, 31, and 32 in different volumes in each compartment 12. This embodiment may e.g. be advantageous when inhibiting the electron transport chain in cells using neurotoxins where the setup requires that the different neurotoxins are dispensed in a certain order and that there is a period of time between dispensing the different types of neurotoxins from the different compartments 12.

Figure 6:
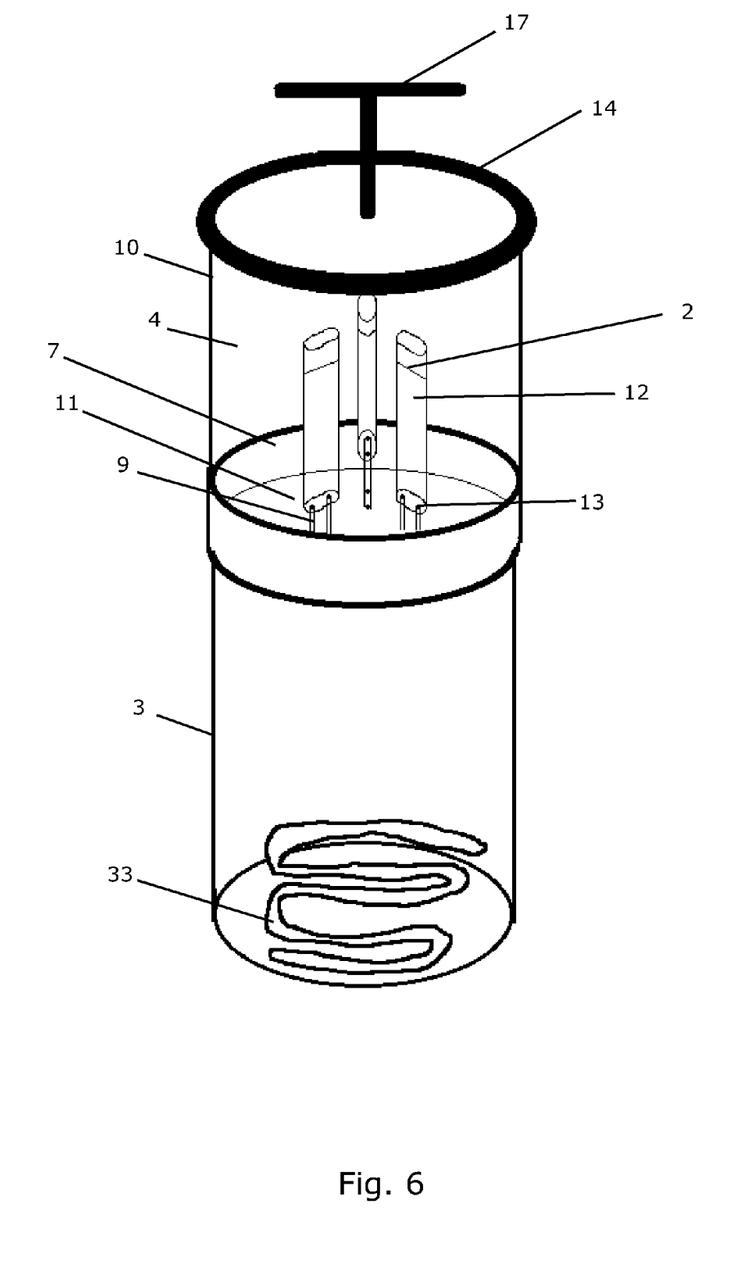
FIG. 6 shows an assembled view of another embodiment of the invention which is a dispensing unit for large volume tissue samples.

The dispensing unit 1 may be designed in different sizes in order to comply with the requirements from the hospitals where both small tissue samples, such as skin samples, as well as large volumes of tissue sample, such as an intestine sample, need to be preserved. In FIG. 6 an embodiment of a dispensing unit for a large volume of tissue sample 33 is shown. It mainly differs from the previously described embodiments in that the dimensions are larger; this is not seen in the figures. Another difference is that the handle 17 is T-shaped in order to have a better grip when rotating the larger unit for dispensing the fluid and applying more force for rotating the reagent cylinder 10 which is necessary for a larger dispensing unit.

Figure 7:
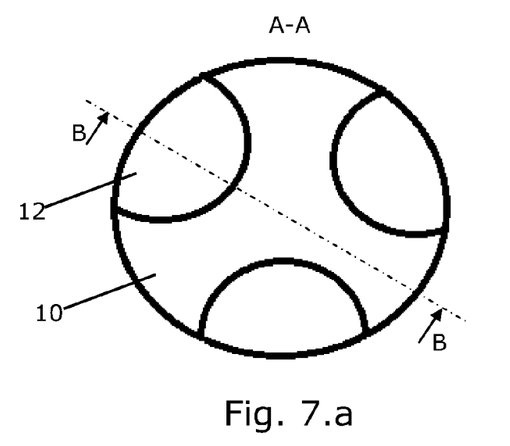
FIG. 7 shows another embodiment of the present invention in which a part of the wall of each compartments is formed by the outer wall of the connector part.

FIG. 7 shows another embodiment of the invention in which the compartments 12 are partly formed as cavities extending from an outer circumference of the reagent cylinder 10, so that closed compartments 12 are not formed until the reagent cylinder 10 is assembled with the connector part 4. Such a design may be advantageous with some manufacturing methods. FIG. 7.*a* is a cross sectional view along line A-A in FIG. 7.*b*, and FIG. 7.*b* is a cross sectional view along line B-B in FIG. 7.*a*. In such an embodiment, O-rings 29 will preferably be arranged at pre-determined locations along the interface between the reagent cylinder 10 and the connector part 4. Such O-rings 29 may e.g. be arranged at the locations shown in FIG. 7. They will typically be arranged in corresponding grooves (not shown) in the connector part 4 and/or the reagent cylinder 10 to make sure that they stay in place.

When the tissue sample 34 has been removed from the external container 3 for analysis, the external container 3 still containing the fluid 2 may be re-fastened to the dispensing unit 1. By turning the assembled dispensing unit 1 and external container 3 upside-down, the fluid can run back into the compartments 12, and the reagent cylinder 10 can then be rotated to a closed position, i.e. with the openings 13 and passages 13 not aligned. The whole assembly including the fluid 2 can then be handled safely, e.g. by sending it away for destruction.

As described above, the dispensing unit may be made in different sizes. For applications within preservation of tissue samples, such as skin samples, typical diameters will be 20-100 mm, such as 20-50 mm or 50 to 100 mm. The height of an assembled container will typically be in the order of 50 to 150 mm, such as 50 to 100 mm or 100 to 200 mm. The total volume of the compartments will typically be in the order of 50 to 100 ml when the dispensing unit is used in relation to preservation of tissue samples. However, as is described above, other dimensions are also covered by the scope of the present invention.

Although the present invention has been described in connection with the specified embodiments, it should not be construed as being in any way limited to the presented examples. For example the dispensing unit has only been illustrated as having three compartments 12, but other numbers of compartments, such as only one, will also be covered by the scope of the present invention. Furthermore, the embodiment described in details relates to preservation of tissue samples 34 by application of a preservation fluid 2, which should be handled with great care due to potential health risks. However, as described in relation to the background of the invention, the invention may also find use in other fields, such as for analysis of water samples. In such applications, it may not be necessary to be able to fasten the dispensing unit to the external container, as it can be manually handled without health risks. For such applications the external container will not contain tissue samples but water samples.

The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A dispensing unit for dispensing fluid into an external container, comprising:
   a connector comprising:
      an upper fastener, and
      a bottom wall having an interior bottom surface, an exterior bottom surface, and at least one passage between the interior bottom surface and the exterior bottom surface,
   a reagent cylinder for storing the fluid, the reagent cylinder being adapted to be rotatably fitted into the connector part, and comprising:
      a cylinder bottom, and
      at least one compartment for storing the fluid, the compartment comprising at least one opening through the cylinder bottom, wherein the at least one opening is located so that for at least one mutual orientation of the reagent cylinder and the connector, the at least one opening is aligned with the at least one passage, and fluid can flow from the compartment to the external container via the at least one opening and the at least one passage,
   a locking ring comprising:
      a second fastener, which attaches to the upper fastener of the connector, so that when the locking ring is tightened, the cylinder bottom of the reagent cylinder is pressed towards the interior bottom surface of the connector and creating a fluid tight sealing between the connector and the reagent cylinder.

2. The dispensing unit according to claim 1, wherein the reagent cylinder comprises more than one compartment for storing one or more types of fluid.

3. The dispensing unit according to claim 2, wherein the connector has the at least one passage arranged so that it is possible to dispose fluid from one compartment at a time.

4. The dispensing unit according to claim 1, wherein each compartment comprises two openings through the cylinder bottom.

5. The dispensing unit according to claim 1, wherein each compartment comprises a seal arranged around the at least one opening of each compartment.

6. The dispensing unit according to claim 1, wherein the connector further comprises a lower fastner, which attaches to the external container.

7. The dispensing unit according to claim 6, wherein the lower fastener of the connector comprises threads or a snap-lock.

8. The dispensing unit according to claim 1, wherein the upper fastener of the connector, and the second fastener of the locking ring comprises threads or a snap-lock.

9. The dispensing unit according to claim 1, wherein each of the connector, the reagent cylinder, and the locking ring comprises a polymer, glass, or metal.

10. The dispensing unit according to claim 1, wherein the connector comprises an outer circular wall forming a space into which the reagent cylinder can be fitted.

11. The dispensing unit according to claim 1, wherein the reagent cylinder comprises a top surface and a handle extending from the top surface, the handle being suitable for manually rotating the reagent cylinder inside the connector part.

12. The dispensing unit according to claim 1, wherein the connector further comprises a removable seal that covers the exterior bottom surface.

13. The dispensing unit according to claim 1, wherein a reagent for preservation of tissue samples is stored in the at least one compartment.

* * * * *